(12) United States Patent
Arrick et al.

(10) Patent No.: US 12,097,021 B2
(45) Date of Patent: Sep. 24, 2024

(54) DRUG DELIVERY DEVICE

(71) Applicants: Massachusetts Institute of Technology, Cambridge, MA (US); Novo Nordisk A/S, Bagsvaerd (DK); The Brigham and Women's Hospital, Inc., Boston, MA (US)

(72) Inventors: Graham Arrick, San Francisco, CA (US); Torben Sebastian Last, Sollentuna (SE); Declan Gwynne, New York, NY (US); Jacob Wainer, Malden, MA (US); Carlo Giovanni Traverso, Newton, MA (US); Drago Sticker, Malmö (SE); Cody Cleveland, København V (DK); Aghiad Ghazal, Copenhagen (DK); Adam Bohr, Copenhagen (DK); Jorrit Jeroen Water, Frederiksberg (DK); Brian Mouridsen, Fredensborg (DK); Jacob Pyung Hwa Jepsen, Copenhagen (DK); Bozhidar Nikolaev Kozhuharov, Søborg (DK); Kim Frandsen, Brøndby Strand (DK); Robert Langer, Newton, MA (US); Yi Lu, Toronto (CA); Niclas Roxhed, Bromma (SE); Siheng You, Somerville, MA (US)

(73) Assignees: Massachusetts Institute of Technology, Cambridge, MA (US); Novo Nordisk A/S, Bagsvaerd (DK); The Brigham and Women's Hospital, Inc., Boston, MA (US)

( * ) Notice: Subject to any disclaimer, the term of this patent is extended or adjusted under 35 U.S.C. 154(b) by 67 days.

(21) Appl. No.: 17/397,785

(22) Filed: Aug. 9, 2021

(65) Prior Publication Data
US 2022/0039686 A1 Feb. 10, 2022

Related U.S. Application Data

(60) Provisional application No. 63/063,807, filed on Aug. 10, 2020.

(30) Foreign Application Priority Data

Oct. 16, 2020 (EP) .................................... 20202279

(51) Int. Cl.
*A61B 5/07* (2006.01)
*A61B 5/00* (2006.01)

(52) U.S. Cl.
CPC .............. *A61B 5/073* (2013.01); *A61B 5/076* (2013.01); *A61B 5/4839* (2013.01)

(58) Field of Classification Search
CPC ........ A61B 5/073; A61B 5/076; A61B 5/4839
See application file for complete search history.

(56) References Cited

U.S. PATENT DOCUMENTS

| | | |
|---|---|---|
| 4,239,040 A | 12/1980 | Hosoya et al. |
| 6,258,062 B1 | 7/2001 | Thielen et al. |

(Continued)

FOREIGN PATENT DOCUMENTS

| | | |
|---|---|---|
| CN | 108836237 A | 11/2018 |
| WO | WO 2020/106704 A2 | 5/2020 |

(Continued)

OTHER PUBLICATIONS

Extended European Search Report and European search opinion in corresponding European Patent Application No. 20202279.4 mailed Apr. 8, 2021 (6 pages).

*Primary Examiner* — Puya Agahi
*Assistant Examiner* — Grace L Rozanski
(74) *Attorney, Agent, or Firm* — Finnegan, Henderson, Farabow, Garrett & Dunner LLP

(57) ABSTRACT

A drug delivery device for administration to a subject is provided. In some embodiments, the drug delivery device (Continued)

includes a reservoir containing an active pharmaceutical ingredient and a potential energy source. The drug delivery device also includes a trigger operatively associated with the potential energy source, where the trigger is configured to actuate at a predetermined location within the subject. The drug delivery device also includes a rupturable membrane disposed along a flow path extending between the reservoir and an outlet, where the membrane is configured to rupture when the trigger is actuated. Once the trigger is actuated, the potential energy from the potential energy source may be released to expel the active pharmaceutical ingredient in a jet through the outlet.

45 Claims, 9 Drawing Sheets

(56) References Cited

U.S. PATENT DOCUMENTS

| | | |
|---|---|---|
| 2004/0253304 A1 | 12/2004 | Gross et al. |
| 2006/0216337 A1* | 9/2006 | Van Laar ............... A61M 37/00 424/449 |
| 2008/0121825 A1 | 5/2008 | Trovato |
| 2008/0188837 A1 | 8/2008 | Belsky et al. |
| 2009/0306633 A1 | 12/2009 | Trovato et al. |
| 2010/0049120 A1* | 2/2010 | Dijksman ............... A61P 35/00 604/66 |
| 2017/0246438 A1* | 8/2017 | Aran .................... A61M 31/00 |
| 2018/0070857 A1* | 3/2018 | Jones .................. A61M 31/002 |
| 2019/0282791 A1 | 9/2019 | Jones et al. |

FOREIGN PATENT DOCUMENTS

| | | |
|---|---|---|
| WO | WO 2020/106750 A1 | 5/2020 |
| WO | WO 2020/106754 A1 | 5/2020 |
| WO | WO 2020/106757 A1 | 5/2020 |

* cited by examiner

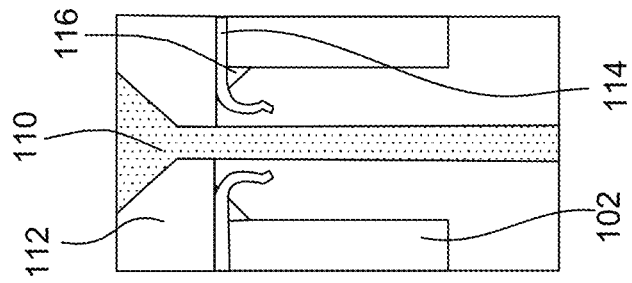
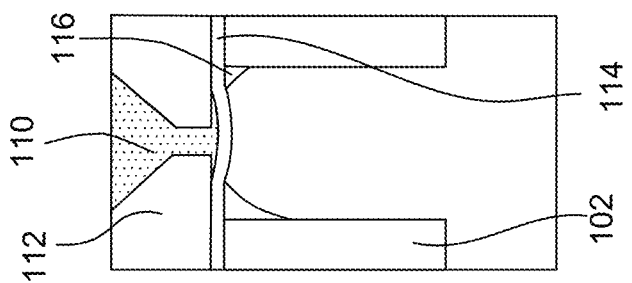
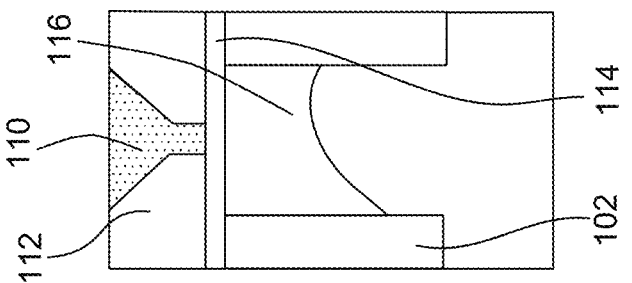
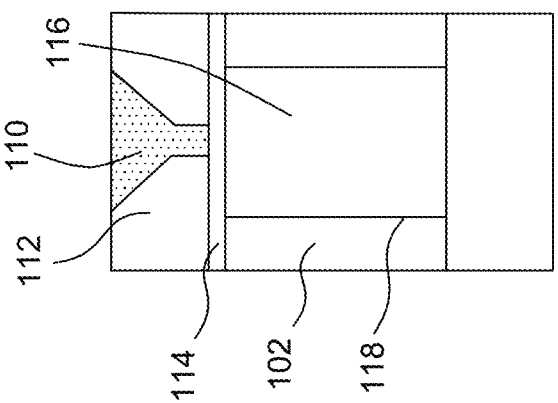

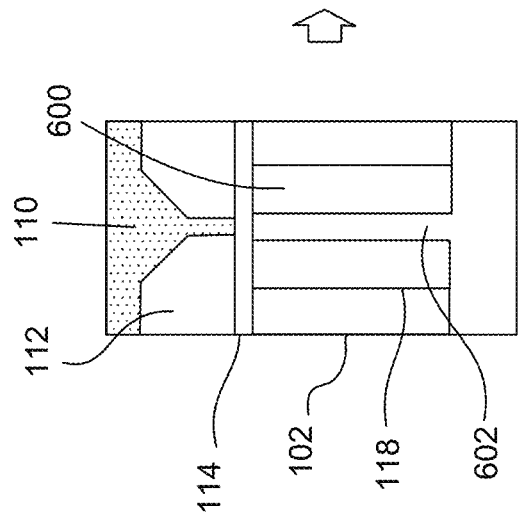

DRUG DELIVERY DEVICE

CROSS-REFERENCE TO RELATED APPLICATIONS

This application claims the benefit of priority of U.S. Provisional Application No. 63/063,807, filed Aug. 10, 2020, and European Patent Application No. 20202279.4, filed Oct. 16, 2020, all of which are incorporated herein by reference in their entireties.

FIELD

Disclosed embodiments are related to drug delivery devices and related methods of use.

BACKGROUND

Certain therapeutics are composed of large and complex molecules that denature readily when administered via the oral-gastrointestinal (GI) route. Accordingly, patients who need these therapeutics typically use more invasive forms of drug administration that are outside the GI route including, for example, subcutaneous injection.

SUMMARY

An ingestible, insertable, or implantable drug delivery device configured for administration to a subject, according to an aspect of the present disclosure, is provided.

In the context of the present disclosure, the term insertable is intended to encompass administration of the drug delivery device endoscopically, rectally, vaginally, nasally or uretherally.

Exemplary advantageous features of the present disclosure are described in the detailed description.

In some embodiments, an ingestible, insertable, or implantable drug delivery device configured for administration to a subject includes a reservoir configured to contain an active pharmaceutical ingredient, a potential energy source, a trigger operatively associated with the potential energy source, where the trigger is configured to actuate in response to one or more predetermined conditions, an outlet in fluid communication with the reservoir, and a rupturable membrane disposed along a flow path extending between the reservoir and the outlet, the rupturable membrane sealing the reservoir from the outlet. When the trigger is actuated, the potential energy source ruptures the rupturable membrane so that the active pharmaceutical ingredient flows from the reservoir via the flow path. The flow path has a first maximum transverse dimension downstream of the rupturable membrane that is larger than a second maximum transverse dimension of the flow path upstream of the rupturable membrane.

In some embodiments, an ingestible, insertable, or implantable drug delivery device configured for administration to a subject includes a reservoir configured to contain an active pharmaceutical ingredient, a potential energy source, a trigger operatively associated with the potential energy source, where the trigger is configured to actuate in response to one or more predetermined conditions, an outlet in fluid communication with the reservoir, and a rupturable membrane disposed along a flow path extending between the reservoir and the outlet, where the rupturable membrane seals the reservoir from the outlet. When the trigger is actuated, the potential energy source compresses the reservoir to rupture the rupturable membrane and flow the active pharmaceutical ingredient from the reservoir through the outlet. The flow path has a first maximum transverse dimension downstream of the rupturable membrane that is larger than a second maximum transverse dimension of the flow path upstream of the rupturable membrane so that the rupturable membrane ruptures in a center portion of the rupturable membrane.

In some embodiments, an ingestible, insertable, or implantable drug delivery device configured for administration to a subject includes a reservoir configured to contain an active pharmaceutical ingredient, a potential energy source, a trigger operatively associated with the potential energy source, where the trigger is configured to actuate in response to one or more predetermined conditions, a first channel in fluid communication with the reservoir, a second channel downstream from the first channel, where the first channel has a first maximum transverse dimension and the second channel has a second maximum transverse dimension larger than the first maximum transverse dimension, and a rupturable membrane disposed between the first channel and the second channel.

It will be appreciated that the nomenclature of the first channel and the second channel is not limiting and that these terms might be interchanged, the second channel being referred to as the first channel and the first channel being referred to as the second channel, for example.

Similarly, it will be appreciated that the nomenclature of the first maximum transverse dimension and the second maximum transverse dimension is not limiting and that these terms might be interchanged, the second maximum transverse dimension being referred to as the first maximum transverse dimension and the first maximum transverse dimension being referred to as the second maximum transverse dimension, for example.

In some embodiments, an ingestible, insertable, or implantable drug delivery device configured for administration to a subject includes a reservoir configured to contain an active pharmaceutical ingredient, a potential energy source, an outlet in fluid communication with the reservoir, a rupturable membrane disposed along a flow path extending between the reservoir and the outlet, and a dissolvable trigger operatively associated with the potential energy source and disposed within the outlet. The dissolvable trigger is configured to dissolve at a predetermined location within the subject while in vivo, and the dissolvable trigger is disposed against and supports a downstream surface of the rupturable membrane.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 2A depicts one embodiment of a drug delivery device rupturable membrane and trigger in a first state;

FIG. 2B depicts the rupturable membrane and trigger of FIG. 2A in a second state;

FIG. 2C depicts the rupturable membrane and trigger of FIG. 2A in a third state;

FIG. 2D depicts the rupturable membrane and trigger of FIG. 2A in a fourth state;

FIG. 7A depicts a schematic of another embodiment of a drug delivery device rupturable membrane and trigger in a first state;

FIG. 7B depicts the rupturable membrane and trigger of FIG. 7A in a second state;

FIG. 7C depicts the rupturable membrane and trigger of FIG. 7A in a third state;

FIG. 7D depicts the rupturable membrane and trigger of FIG. 7A in a fourth state;

DETAILED DESCRIPTION

Figure 1A:
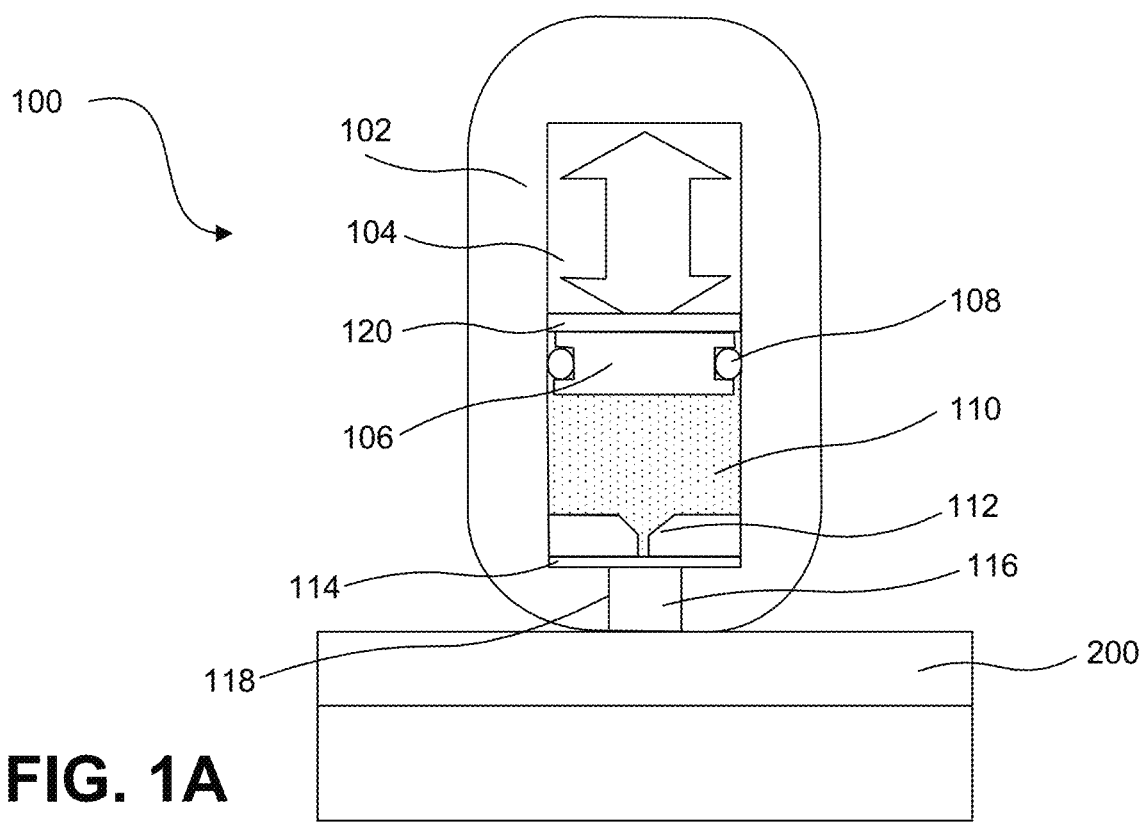
FIG. 1A depicts a schematic of one embodiment of a drug delivery device in a first state.

Large and complex molecules that denature readily when administered via the oral-gastrointestinal (GI) route are regularly administered as a part of therapeutic treatments. Patients requiring these therapeutics oftentimes must use more invasive forms of drug administration such as subcutaneous injection. The use of these more invasive forms of delivery sometimes lead to lapses in routine adherence and/or reduced quality of life.

In view of the above, the inventors have recognized the benefits of ingestible delivery devices that leverage needleless micro-jets to deliver a dose of a desired active pharmaceutical ingredient (API) at a desired location along the gastrointestinal (GI) tract without compromising drug-purity, efficacy, and/or dosage. In particular, the inventors have recognized the benefits of an ingestible delivery devise employing a trigger that automatically releases a dose at a desired location within the GI tract. As used herein, the GI tract includes the esophagus, the stomach, the duodenum, the jejunum, the small intestine, and the large intestine. The delivery device is suitable to delivery of large and complex molecules, such as proteins and other biologics, that may otherwise be unsuitable for delivery through the GI tract, though any appropriate API may be used. According to exemplary embodiments described herein, an ingestible delivery device employing micro-jetting for delivery of an active pharmaceutical ingredient (API) has many potential benefits. First, an ingestible delivery device according to exemplary embodiments described herein may not include sharp points. Second, micro-jects obviate the mechanisms associated with actuating and/or retracting a needle, thereby reducing system complexity and cost relative to needle-based systems. Lastly, implementation of needle-free delivery systems of exemplary embodiments described herein may result in less pain and/or trauma at the site of injection relative to needle-based delivery, as well as enhanced pharmacokinetics (PK).

In some cases, effective implementation of a needle-free drug delivery device may be based at least in part on contact with the subject tissue, as well as a triggering mechanism. While in subcutaneous systems contact is guaranteed by manual placement of the jetting nozzle against the skin, with an ingestible device, neither manual localization nor triggering is possible. Jetting performance of the drug delivery device may also affect the efficacy of an API delivery to a patient.

In view of the above, the inventors have also recognized the benefits of a robust triggering system for a drug delivery device deployed in a GI tract of a patient. In particular, the inventors have recognized the benefits of a rupturable (i.e., frangible) membrane that seals a reservoir containing an API. The rupturable membrane may be physically supported by a trigger such as a sugar plug, an enteric coating, or other dissolvable trigger configured to be dissolved in the GI tract after a predetermined time period and/or at a predetermined location of the GI tract while located in vivo. When the trigger activates, the membrane may rupture to release a controlled micro-jet of the API into the GI mucosal lining. The inventors have recognized the particular benefits of an abrupt transition between upstream and downstream fluid pathways relative to the rupturable membrane. More specifically, in some embodiments, the inventors have recognized the benefits of a flow path having a first maximum transverse dimension (e.g., first maximum diameter) downstream of the rupturable membrane that is larger than a second maximum transverse dimension (e.g., second maximum diameter) of the flow path upstream of the rupturable membrane. Such an arrangement may facilitate the membrane rupturing in a center portion of the membrane rather than at an edge location adjacent to a stress concentration. Without wishing to be bound by theory, providing such a functionality may help ensure a consistent reproducible jet having appropriate penetration characteristics to deliver the API to the GI mucosal lining.

In some embodiments, a drug delivery device configured for administration to a subject includes a reservoir configured to contain an API, a potential energy source, and a trigger configured to actuate at a predetermined location within the subject. The reservoir may be a liquid reservoir and may contain a solution containing the API in a predetermined dosage. The potential energy source may store energy inside of the drug delivery device to be released when the trigger is actuated. The drug delivery device may also include an outlet in fluid communication with the reservoir, and a rupturable membrane positioned along a flow path extending between the reservoir and the outlet. The rupturable membrane may seal the reservoir from the outlet, so that the API is contained inside of the reservoir until the membrane is ruptured. The potential energy source may pressurize or otherwise compress the reservoir to apply a pressure to the rupturable membrane. When the trigger is actuated, the rupturable membrane may rupture to allow the API to flow through the flow path and out of the outlet. The flow path of the drug delivery device may have a first maximum transverse dimension (e.g., first maximum diameter) downstream of the rupturable membrane that is larger than a second maximum transverse dimension (e.g., second maximum diameter) of the flow path upstream of the rupturable membrane so that the pressure applied to the membrane is applied in a center portion of the membrane that is removed from an outer edge of the membrane. In some embodiments, the rupturable membrane may define a transition between the first diameter and the second diameter, such that the flow path has non-continuous walls and the flow path steps from the first diameter to the second diameter at the rupturable membrane. While according to exemplary embodiments described herein a drug delivery device may generate an incompressible liquid jet, in other embodiments a jet generated by a drug delivery device may be formed of gases, viscous fluids, aerosolized powders, and/or other appropriate materials, as the present disclosure is not so limited.

As used herein, a jet refers to a collimated flow of gas, viscous fluids, aerosolized powders, and/or other appropriate materials.

According to exemplary embodiments described herein, a rupturable membrane of a drug delivery device may be formed of a frangible material that is configured to rupture or otherwise break when an unsupported threshold pressure is applied to the membrane. In some embodiments, the rupturable membrane comprises one or more materials chosen from a metal, a polymeric material, an elastomeric material, a plastic material, a ceramic material, a composite material, and/or any other appropriate frangible or brittle material for delivering an active API to a subject. In some embodiments, the rupturable membrane comprises a metal foil, an elastomeric film, a rigid plastic film, a flexible plastic film, and/or any other appropriate material capable of rupturing when a threshold pressure for a given membrane is applied. In some embodiments, the metal is aluminum. In some embodiments, the metal is a biodegradable metal, such as iron. In some embodiments, the plastic material is a reinforce plastic material. In some embodiments, the composite material comprises carbon fibers. In some embodiments, a material for a rupturable membrane may be selected to promote a brittle failure of the membrane during actuation. The rupturable membrane may be configured to rupture in such a manner that a jet of fluid is formed by the drug delivery device. In some embodiments, a rupturable membrane may be configured to function as a nozzle defining a jet exiting a drug delivery device. Of course, a rupturable membrane may be formed of any suitable material configured to rupture when a trigger of the drug delivery device actuates, as the present disclosure is not so limited. According to exemplary embodiments described herein, a rupturable membrane may have a thickness less than or equal to 150 µm, 100 µm, 75 µm, 50 µm, 25 µm, 15 µm, and/or any other appropriate thickness. Correspondingly, a rupturable membrane may have a thickness greater than or equal to 10 µm, 15 µm, 25 µm, 50 µm, 75 µm, and/or any other appropriate thickness. Combinations of the above-noted ranges are contemplated, including thicknesses between 10 µm and 25 µm, between 10 µm and 50 µm, between 10 µm and 75 µm, between 10 µm and 100 µm, between 10 µm and 150 µm, between 15 µm and 25 µm, between 15 µm and 50 µm, between 15 µm and 75 µm, between 15 µm and 100 µm, between 15 µm and 150 µm, between 25 µm and 50 µm, between 25 µm and 100 µm, between 25 µm and 150 µm, between 25 µm and 75 µm, between 50 µm and 75 µm, between 50 µm and 100 µm, between 50 µm and 150 µm, between 75 µm and 100 µm, between 75 µm and 150 µm, or between 100 µm and 150 µm. As described herein, the phrase "between one value and another value" includes the endpoints and all values between the endpoints.

According to exemplary embodiments described herein, a trigger of a drug delivery device may be configured to actuate the drug delivery device in the GI tract of a subject under a predetermined condition. In some embodiments, the predetermined condition includes one or more of a predetermined time after ingestion of the drug delivery device, a predetermined location in the GI tract, physical contact with the GI tract, physical manipulation in the GI tract (e.g., compression via peristalsis), one or more characteristics of the GI tract (e.g., pH, pressure, acidity, temperature, etc.), or combinations thereof. In some embodiments, the trigger may be a passive component configured to interact with the environment of the GI tract to actuate the drug delivery device. For example, in some embodiments the trigger may be a sugar plug, or other dissolvable material, configured to dissolve in the GI tract. The dissolvable plug may have a certain thickness and/or shape that at least partly determines the speed at which the sugar plug dissolves and ultimately actuates the drug delivery device. In some embodiments, the trigger has an oval shape, an egg shape, a spherical shape, an elliptical shape, a cylindrical shape, a conical shape, or a spherocylindrical shape. In another embodiment, the trigger may be at least partially formed by an enteric coating. For example, in some embodiments, a trigger may include both a sugar plug and an enteric coating, as the present disclosure is not so limited. Other appropriate materials for a dissolvable trigger may include, but are not limited to, sugar alcohols, such as disaccharides (e.g. Isomalt), water soluble polymers, such as Poly-vinyl alcohol, enteric coatings, time-dependent coatings, enteric and time-dependent coatings, temperature-dependent coatings, light-dependent coatings, and/or any other appropriate material capable of being dissolved within the GI tract of a subject. In some embodiments, a trigger may include a triggerable membrane including EDTA, glutathione, or another suitable chemical. In some embodiments, a sugar alcohol trigger may be employed in combination with an enteric coating configured to protect the sugar alcohol trigger until the drug delivery device is received in the GI tract of a subject. In some embodiments, the trigger may include a pH responsive coating to assist with delaying triggering until after ingestion. In some embodiments, the trigger may be a sensor that detects one or more characteristics of the GI tract. For example, a sensor detecting contact with a GI mucosal lining may be used to actuate the device. In embodiments where a sensor is employed, the trigger may also include an active component that moves in response to a predetermined condition being detected by the sensor. For example, a gate may be moved when contact with a GI mucosal tract is detected. In other embodiments the trigger may employ electrical power to melt or weaken a rupturable membrane (e.g., by applying a voltage across a conductive rupturable membrane) and/or trigger a chemical reaction. Of course, any suitable active or passive trigger may be employed for a drug delivery device, as the present disclosure is not so limited.

According to exemplary embodiments described herein, a drug delivery device includes a potential energy source which is used to store energy in the drug delivery device that is used to generate a jet of an API when the drug delivery device is actuated. In some embodiment, the potential energy source may be a compressed gas. The compressed gas may be directly stored in the drug delivery device, or the compressed gas may be generated via a chemical reaction or phase change. For example, in some embodiments, dry ice may be stored in a chamber of the drug delivery device so that compressed gas is generated as the dry ice sublimates. Alternatively, a compressed gas may be provided to a desired chamber prior to sealing a drug delivery device. In some embodiments, the potential energy source may be a spring (e.g., a compressed compression spring). In some embodiments, the potential energy source may be a reaction chamber. For example, the reaction chamber may allow an acid and base to be combined to generate gas, leading to the expulsion of API from the drug delivery device when the trigger is actuated. Alternatively, in another embodiment, a trigger may detonate an explosive material located within a chamber to generate pressurized gas for expelling the API from the drug delivery device. Of course, any suitable reaction or other potential energy source may be employed to pressurize and drive an API in a jet when a drug delivery device is actuated, as the present disclosure is not so limited.

Without wishing to be bound by theory, jetting power may be tuned to delivery an API into different target tissues within the GI tract with different penetration characteristics. Jetting power may be at least partly determined by jet velocity, fluid density, and jet diameter. Accordingly, a drug delivery device according to exemplary embodiments described herein may be appropriately sized and include an appropriate amount of potential energy to generate a jet with enough power to deliver an API to the GI mucosal lining in a desired location.

As noted above, jetting power of a drug delivery device may affect the efficacy of API delivery to a GI mucosal lining. Accordingly, a drug delivery device may employ an appropriate jetting power and velocity to penetrate a GI mucosal lining and deliver an API to a subject. In some embodiments, jetting power for a drug delivery device according to exemplary embodiments described herein is less than or equal to 250 W, 200 W, 150 W, 100 W, 75 W, 50 W, 20 W, 10 W, 5 W, 1 W, 100 mW, and/or any other suitable power. Correspondingly, a jetting power for a drug delivery device may be greater than or equal to 50 mW, 100 mW, 1 W, 5 W, 10 W, 20 W, 50 W, 75 W, 100 W, 150 W, 200 W, and/or any other suitable power. Combinations of the above noted ranges are contemplated, including jetting powers between 50 mW and 250 W, between 50 mW and 200 W, between 50 mW and 150 W, between 50 mW and 100 W, between 50 mW and 75 W, between 50 mW and 50 W, between 50 mW and 20 W, between 50 mW and 10 W, between 50 mW and 5 W, between 50 mW and 1 W, between 100 mW and 200 W, between 100 mW and 150 W, between 100 mW and 100 W, between 100 mW and 75 W, between 100 mW and 50 W, between 100 mW and 20 W, between 100 mW and 10 W, between 100 mW and 5 W, between 100 mW and 1 W, between 1 W and 200 W, between 1 W and 150 W, between 1 W and 100 W, between 1 W and 75 W, between 1 W and 50 W, between 1 W and 20 W, between 1 W and 10 W, between 1 W and 5 W, between 5 W and 200 W, between 5 W and 150 W, between 5 W and 100 W, between 5 W and 75 W, between 5 W and 50 W, between 5 W and 20 W, between 5 W and 10 W, between 10 W and 200 W, between 10 W and 150 W, between 10 W and 100 W, between 10 W and 75 W, between 10 W and 50 W, between 10 W and 20 W, between 20 W and 200 W, between 20 W and 150 W, between 20 W and 100 W, between 20 W and 75 W, between 20 W and 50 W, between 50 W and 200 W, between 50 W and 150 W, between 50 W and 100 W, between 50 W and 75 W, between 75 W and 200 W, between 75 W and 150 W, between 75 W and 100 W, between 75 W and 200 W, between 75 W and 150 W, between 75 W and 100 W, between 100 W and 200 W, between 100 W and 150 W, or between 150 W and 200 W. Of course, any jetting power suitable to deliver an API to a GI mucosal lining may be employed, as the present disclosure is not so limited.

To achieve the exemplary jetting powers described herein, a jet generated by a drug delivery device of exemplary embodiments described herein may have a corresponding velocity. Accordingly, in some embodiments, a drug delivery device may be configured to generate a jet having a velocity less than or equal to 250 m/s, 200 m/s, 150 m/s, 100 m/s, 75 m/s, 50 m/s, and/or another appropriate velocity. Correspondingly, a drug delivery device may be configured to generate a jet having a velocity greater than or equal to 20 m/s, 30 m/s, 50 m/s, 100 m/s, 150 m/s, 200 m/s, and/or another appropriate velocity. Combinations of the above-noted ranges are contemplated, including, but not limited to, jet velocities between 20 m/s and 250 m/s, between 20 m/s and 200 m/s, between 20 m/s and 100 m/s, between 20 m/s and 150 m/s, between 20 m/s and 100 m/s, between 20 m/s and 75 m/s, between 20 m/s and 50 m/s, between 50 m/s and 250 m/s, between 50 m/s and 200 m/s, between 50 m/s and 100 m/s, between 50 m/s and 150 m/s, between 50 m/s and 100 m/s, between 50 m/s and 75 m/s, between 75 m/s and 250 m/s, between 75 m/s and 200 m/s, between 75 m/s and 100 m/s, between 75 m/s and 150 m/s, between 75 m/s and 100 m/s, between 100 m/s and 250 m/s, between 100 m/s and 200 m/s, between 100 m/s and 150 m/s, between 150 m/s and 250 m/s, between 150 m/s and 200 m/s, or between 200 m/s and 250 m/s. Of course, any jet velocity suitable to deliver an API to a GI mucosal lining, or other structure associated with the GI tract of a subject, may be employed, as the present disclosure is not so limited.

In some embodiments, a maximum transverse dimension of an outlet and/or jet (e.g. a diameter) may be less than or equal to 600 μm, 350 μm, 300 μm, 250 μm, 200 μm, 150 μm, 100 μm, 75 μm, 50 μm, 25 μm, 10 μm, and/or any other appropriate dimension. Correspondingly, an outlet and/or jet maximum transverse dimension may be greater than or equal to 5 μm, 10 μm, 25 μm, 50 μm, 75 μm, 100 μm, 150 μm, 200 μm, 250 μm, 300 μm, 600 μm and/or any other appropriate dimension. Combinations of the above-noted ranges are contemplated, including, but not limited to, maximum transverse dimensions of a jet and/or outlet between 5 μm and 600 μm, between 10 μm and 600 μm, between 25 μm and 600 μm, between 50 μm and 600 μm, between 75 μm and 600 μm, between 100 μm and 600 μm, between 150 μm and 600 μm, between 200 μm and 600 μm, between 250 μm and 600 μm, between 300 μm and 600 μm, between 350 μm and 600 μm, between 5 μm and 350 μm, between 10 μm and 350 μm, between 25 μm and 350 μm, between 50 μm and 350 μm, between 75 μm and 350 μm, between 100 μm and 350 μm, between 150 μm and 350 μm, between 200 μm and 350 μm, between 250 μm and 350 μm, between 300 μm and 350 μm, between 5 μm and 300 μm, between 10 μm and 300 μm, between 25 μm and 300 μm, between 50 μm and 300 μm, between 75 μm and 300 μm, between 100 μm and 300 μm, between 150 μm and 300 μm, between 200 μm and 300 μm, between 250 μm and 300 μm, between 5 μm and 250 μm, between 10 μm and 250 μm, between 25 μm and 250 μm, between 50 μm and 250 μm, between 75 μm and 250 μm, between 100 μm and 250 μm, between 150 μm and 250 μm, between 200 μm and 250 μm, between 5 μm and 200 μm, between 10 μm and 200 μm, between 25 μm and 200 μm, between 50 μm and 200 μm, between 75 μm and 200 μm, between 100 μm and 200 μm, between 150 μm and 200 μm, between 5 μm and 150 μm, between 10 μm and 150 μm, between 25 μm and 150 μm, between 50 μm and 150 μm, between 75 μm and 150 μm, between 100 μm and 150 μm, between 5 μm and 100 μm, between 10 μm and 100 μm, between 25 μm and 100 μm, between 50 μm and 100 μm, between 75 μm and 100 μm, between 5 μm and 75 μm, between 10 μm and 75 μm, between 25 μm and 75 μm, between 50 μm and 75 μm, between 5 μm and 50 μm, between 10 μm and 50 μm, between 25 μm and 50 μm, between 5 μm and 25 μm, between 10 μm and 25 μm, or between 5 μm and 10 μm. Of course, any jet diameter suitable for delivery of an API to a GI mucosal lining may be employed, as the present disclosure is not so limited.

According to exemplary embodiments described herein, a drug delivery device includes a potential energy source configured to pressurize an API so that the API may be released in a jet into a GI tract mucosal lining. The pressure applied to the reservoir may affect jetting power and/or a jet velocity of an API jet emitted by the drug delivery device. In some embodiments, the potential energy source may apply a pressure to an API reservoir less than or equal to 1000 bar, 800 bar, 600 bar, 500 bar, 250 bar, 100 bar, 60 bar, 40 bar, 10 bar, 1 bar, and/or any other appropriate pressure. Correspondingly, the potential energy source may apply a pressure to an API reservoir greater than or equal to 0.1 bar, 1 bar, 10 bar, 40 bar, 60 bar, 100 bar, 250 bar, 500 bar, 600 bar, 800 bar, and/or any other appropriate pressure. Combinations of the above-noted ranged are contemplated, including, but not limited to, pressures between 0.1 bar and 1000 bar, between 0.1 bar and 800 bar, between 0.1 bar and 600 bar, between 0.1 bar and 500 bar, between 0.1 bar and 250 bar, between 0.1 bar and 100 bar, between 0.1 bar and 60 bar, between 0.1 bar and 40 bar, between 0.1 bar and 10 bar, between 0.1 bar and 1 bar, between 1 bar and 1000 bar, between 1 bar and 800 bar, between 1 bar and 600 bar, between 1 bar and 500 bar, between 1 bar and 250 bar, between 1 bar and 100 bar, between 1 bar and 60 bar, between 1 bar and 40 bar, between 1 bar and 10 bar, between 10 bar and 1000 bar, between 10 bar and 800 bar, between 10 bar and 600 bar, between 10 bar and 500 bar, between 10 bar and 250 bar, between 10 bar and 100 bar, between 10 bar and 60 bar, between 10 bar and 40 bar, between 10 bar and 800 bar, between 10 bar and 600 bar, between 10 bar and 500 bar, between 10 bar and 250 bar, between 10 bar and 100 bar, between 10 bar and 60 bar, between 10 bar and 40 bar, between 40 bar and 800 bar, between 40 bar and 600 bar, between 40 bar and 500 bar, between 40 bar and 250 bar, between 40 bar and 100 bar, between 40 bar and 60 bar, between 60 bar and 800 bar, between 60 bar and 600 bar, between 60 bar and 500 bar, between 60 bar and 250 bar, between 60 bar and 100 bar, between 100 bar and 800 bar, between 100 bar and 600 bar, between 100 bar and 500 bar, between 100 bar and 250 bar, between 250 bar and 800 bar, between 250 bar and 600 bar, between 250 bar and 500 bar, between 500 bar and 800 bar, between 500 bar and 600 bar, or between 600 bar and 800 bar. Of course, any suitable pressure may be applied to an API reservoir, as the present disclosure is not so limited.

A drug delivery device of exemplary embodiments described herein may be configured to deliver a predetermined dose of an API to a subject. According to exemplary embodiments described herein, a drug delivery device may include an API reservoir volume less than or equal to 500 μL, 300 μL, 200 μL, 150 μL, 100 μL, 75 μL, 50 μL, 25 μL, 10 μL, and/or any other appropriate volume. Correspondingly, a drug delivery device may contain an API reservoir volume greater than or equal to 1 μL, 5 μL, 10 μL, 25 μL, 50 μL, 75 μL, 100 μL, 200 μL, 300 μL, and/or any other appropriate volume. Combinations of the above-noted volumes are contemplated, including, but not limited to, reservoir volumes between 1 μL and 500 μL, between 1 μL and 300 μL, between 1 μL and 200 μL, between 1 μL and 150 μL, between 1 μL and 100 μL, between 1 μL and 75 μL, between 1 μL and 50 μL, between 1 μL, and 25 μL, between 1 μL and 10 μL, between 10 μL and 500 μL, between 10 μL and 300 μL, between 10 μL and 200 μL, between 10 μL and 150 μL, between 10 μL and 100 μL, between 10 μL and 75 μL, 10 μL and 50 μL, between 10 μL and 25 μL, between 25 μL and 500 μL, between 25 μL and 300 μL, between 25 μL and 200 μL, between 25 μL and 150 μL, between 25 μL and 100 μL, between 25 μL and 75 μL, between 25 μL and 50 μL, between 50 μL and 500 μL, between 50 μL and 300 μL, between 50 μL and 200 μL, between 50 μL and 150 μL, between 50 μL and 100 μL, between 50 μL and 75 μL, between 75 μL and 500 μL, between 75 μL and 300 μL, between 75 μL and 200 μL, between 75 μL and 150 μL, between 75 and 100 between 100 μL and 500 μL, between 100 μL and 300 μL, between 100 μL and 200 μL, between 100 μL and 150 μL, between 150 μL and 500 μL, between 150 μL and 300 μL, between 150 μL and 200 μL, between 200 μL and 500 μL, between 200 μL and 300 μL, or between 300 μL and 500 μL. Of course, any suitable reservoir volume may be employed in a drug delivery device, as the present disclosure is not so limited.

In some embodiments, a drug delivery device is sized and shaped to be ingested by a subject. Accordingly, the drug delivery device may be appropriately small so that the drug delivery device may be easily swallowed and subsequently pass through the GI tract, including the esophagus and pyloric opening within the stomach. In some embodiments, a drug delivery device may include an overall length, such as a maximum dimension along a longitudinal axis of the device, that is less than or equal to 40 mm, 30 mm, 20 mm, 10 mm, 5 mm, and/or another appropriate length. Correspondingly, a drug delivery device may have an overall length greater than or equal to 3 mm, 5 mm, 10 mm, 20 mm, 25 mm, and/or another appropriate length. Combinations of the above-noted ranges are contemplated, including, but not limited to, overall lengths between 5 mm and 30 mm, between 10 mm and 30 mm, between 20 mm and 30 mm, between 25 mm and 30 mm, between 5 mm and 25 mm, between 10 mm and 25 mm, between 20 mm and 25 mm, between 5 mm and 20 mm, between 10 mm. In some embodiments, a drug delivery device may have a maximum external transverse dimension, such as a diameter or other dimension that may be perpendicular to the longitudinal axis, that is less than or equal to 11 mm, 10 mm, 7 mm, 5 mm, and/or another appropriate dimension. Correspondingly, a drug delivery device may have a maximum external transverse dimension greater than or equal to 3 mm, 5 mm, 7 mm, 9 mm, and/or another appropriate dimension. Combinations of the above-noted ranges are contemplated, including, but not limited to, maximum external transverse dimensions between 3 mm and 11 mm, between 3 mm and 10 mm, between 3 mm and 7 mm, between 3 mm and 5 mm, between 5 mm and 11 mm. In some embodiments, a drug delivery device may have an overall volume less than or equal to 3500 $mm^3$, 3000 $mm^3$, 2500 $mm^3$, 2000 $mm^3$, 1500 $mm^3$, 1000 $mm^3$, 750 $mm^3$, 500 $mm^3$, 250 $mm^3$, 100 $mm^3$, and/or any other appropriate volume. Corresponding, a drug delivery device may have an overall volume greater than or equal to 50 $mm^3$, 100 $mm^3$, 250 $mm^3$, 500 $mm^3$, 750 $mm^3$, 1000 $mm^3$, 1500 $mm^3$, 2000 $mm^3$, 2500 $mm^3$, and/or any other appropriate volume. Combinations of the above-noted ranged are contemplated, including, but not limited to, volumes between 1000 $mm^3$ and 3000 $mm^3$, 1500 $mm^3$ and 3000 $mm^3$, 50 $mm^3$ and 500 $mm^3$, 50 $mm^3$ and 100 $mm^3$, as well as 2000 $mm^3$ and 3000 $mm^3$. Of course, any suitable overall length, maximum external transverse dimension, and volume for an ingestible delivery device may be employed, as the present disclosure is not so limited.

According to exemplary embodiments described herein, the drug delivery device is administered to a subject orally. In other embodiments, the drug delivery device may be administered, endoscopically, rectally, vaginally, nasally, or uretherally, as the present disclosure is not so limited. Additionally, in some cases a drug delivery device according to exemplary embodiments described herein may be implanted into an organ of a subject. For example, a drug delivery device may be implanted into the arm, brain, peritoneum, etc. of the subject.

In some embodiments, it may be desirable to orient an outlet of a jet towards a surface of the GI tract of a subject prior to actuating a delivery device to help ensure delivery of an API into the desired tissue. Accordingly, depending on the particular embodiment, a variety of different strategies may be employed. For example, various mucoadhesives, dissolvable hooks for attaching to tissue, mucosal contact sensors, and other methods of either maintaining a delivery device in contact with and/or determining when they delivery device is proximate to a desired tissue within a GI tract may be used. For example, various self-righting or self-orienting structures and/or methods described in WO 2018/213600 A1 can be employed by the drug delivery device in accordance with the present disclosure. WO 2018/213600 A1 is incorporated herein by reference in its entirety. Additionally, in some embodiments, multiple outlets and corresponding multiple jets located at different positions on an exterior of the delivery device may be used to increase the chance of one of the jets being oriented towards a tissue proximate to the delivery device. Of course, it should be understood that embodiments in which a delivery device does not include sensors for sensing contact with and/or a component for attaching to a mucosal lining of a subject are also contemplated.

As used herein, the term "active pharmaceutical ingredient" (also referred to as a "drug" or "therapeutic agent") refers to an agent that is administered to a subject to treat a disease, disorder, or other clinically recognized condition, or for prophylactic purposes, and has a clinically significant effect on the body of the subject to treat, prevent, and/or diagnose the disease, disorder, or condition. The active pharmaceutical ingredient may be delivered to a subject in a quantity greater than a trace amount to affect a therapeutic response in the subject. In some embodiments, active pharmaceutical ingredients (APIs) can include, but are not limited to, any synthetic or naturally-occurring biologically active compound or composition of matter which, when administered to a subject (e.g., a human or nonhuman animal), induces a desired pharmacologic, immunogenic, and/or physiologic effect by local and/or systemic action. For example, useful or potentially useful within the context of certain embodiments are compounds or chemicals traditionally regarded as drugs, vaccines, and biopharmaceuticals. Certain such APIs may include molecules such as proteins, peptides, hormones, nucleic acids, gene constructs, etc., for use in therapeutic, diagnostic, and/or enhancement areas. In certain embodiments, the API is a small molecule and/or a large molecule. Accordingly, it should be understood that the API's described herein are not limited to any particular type of API.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1A depicts a schematic of one embodiment of a drug delivery device 100 in a first state representative of a state prior to actuation of the drug delivery device 100. As shown in FIG. 1A, the drug delivery device 100 includes a housing 102 containing a potential energy source configured as a compressed gas compartment 104 and an active pharmaceutical ingredient (API) reservoir 110. The compressed gas compartment 104 and reservoir 110 are separated by a piston 106 slidably received in an interior of the housing 102. The piston 106 includes a piston seal 108 configured to inhibit fluid transfer between the compressed gas compartment 104 and the reservoir 110. The piston 106 transfers pressure from the compressed gas compartment 104 to the reservoir 110. That is, the compressed gas inside of the gas compartment 104 pressurizes the API inside of the reservoir 110. As shown in FIG. 1A, the reservoir 110 is fluidly connected to a nozzle 112 that reduces a maximum transverse dimension of a fluid flow path, which may include a downstream opening of the nozzle, from a transverse dimension of the reservoir to a maximum transverse dimension corresponding to a desired maximum transverse dimension (e.g. a diameter) of a jet. The nozzle 112 is configured to generate a jet of API when the pressurized API flows out of the nozzle 112. The drug delivery device also includes a fluid outlet 118 in fluid communication with the nozzle 112. In the depicted embodiment, a maximum transverse dimension of the outlet is greater than a maximum transverse dimension of a downstream opening formed in the nozzle. A rupturable membrane 114 is positioned between the nozzle 112 and the outlet 118. According to the particular embodiment of FIG. 1A, the rupturable membrane may be formed of a metal foil though other rupturable membranes may also be used. The rupturable membrane is configured to rupture under the pressure of the pressurized API in the reservoir 110. However, the device includes a trigger 116 in the form of a dissolvable plug physically retained within an outlet 118 of the device where the plug is disposed against a surface of the membrane on a side of the membrane opposite the nozzle. The dissolvable plug may be configured to physically support the rupturable membrane prior to being dissolved. Accordingly, while the trigger 116 is positioned in the outlet 118 the rupturable membrane is supported and does not rupture under pressure of the API.

According to the embodiment of FIG. 1A, the drug delivery device 100 includes a diffusion barrier 120 positioned between the gas compartment 104 and the piston 106. The gas diffusion barrier 120 may be configured to prevent diffusion of the gas contained in the gas compartment 104 over time into the API reservoir 110. Additionally, the diffusion barrier 120 may be configured to prevent diffusion of gas contained in the gas compartment 104 over time out of the housing 102. The diffusion barrier 120 may inhibit gas diffusion more so than the piston seal 108 alone, such that the device 100 is suitable for longer shelf storage life. The diffusion barrier 120 may be a rupturable barrier configured to break when the rupturable membrane 114 ruptures. In some embodiments, the diffusion barrier may be formed of a metal foil, though other materials may also be used. Like the rupturable membrane 114, the diffusion barrier 120 may be configured to rupture under the pressure of the gas inside of the gas compartment 104. However, the piston 106 and the underlying fluid in the API reservoir 110 are configured to support the diffusion barrier. That is, the diffusion barrier 120 is supported by the piston 106 until the device 100 is actuated and the rupturable membrane 114 is ruptured. As the piston 106 moves toward the nozzle 112 to expel the API in the API reservoir 110, the support is removed from the diffusion barrier 120 and the diffusion barrier 120 breaks to allow the gas in the gas compartment to continue to apply pressure to the piston 106 (see FIG. 1B).

Figure 1B:
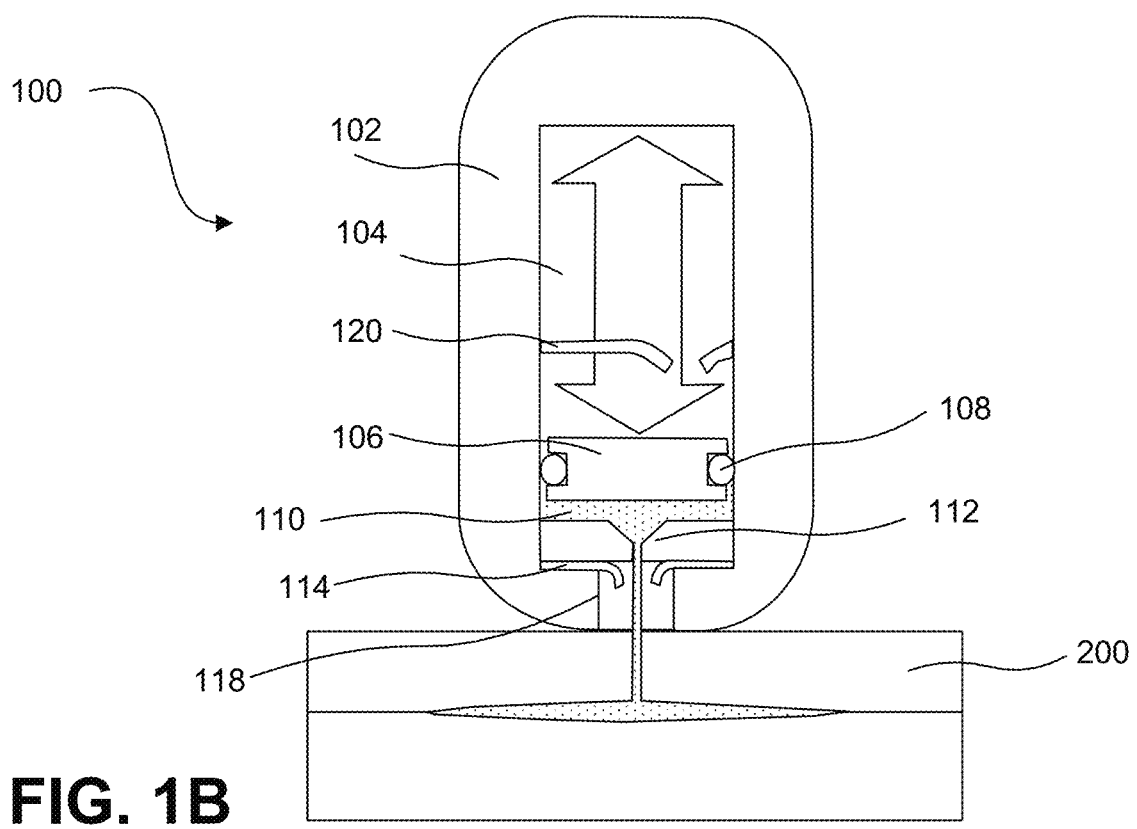
FIG. 1B depicts the drug delivery device of FIG. 1A in a second state.

As shown in FIG. 1B, when the trigger 116 dissolves inside of a GI tract of the subject, the physical support for the rupturable membrane 114 is removed. Accordingly, the pressure from the API through the nozzle 112 applies an unsupported force to the rupturable membrane 114 sufficient to rupture the rupturable membrane 114. Once ruptured, the API flows out of the reservoir 110 in a jet from the nozzle 112 and into GI tract mucosal tissue 200 of a subject. As shown in FIG. 1B, the jet may have an appropriate combination of power, velocity, and diameter to penetrate the tissue 200 to a desired depth. Again, as the piston 106 advances toward the nozzle 112, the diffusion barrier 120 breaks under the pressure of the gas in the gas compartment 104, which is shown by the broken diffusion barrier in FIG. 1B.

According to the embodiment of FIGS. 1A-1B, the nozzle 112 and outlet 118 are configured such that the rupturable membrane 114 reliably ruptures in a center portion of the membrane to ensure consistent jetting performance. Specifically, as shown in FIGS. 1A-1B, the nozzle 112 has an exit port flow path adjacent the membrane having a first diameter (e.g., first maximum transverse dimension). The outlet 118 has a second diameter (e.g., second maximum transverse dimension) that is larger than the first diameter. Accordingly, a flow path upstream of the membrane 114 has a diameter less than a diameter of a flow path downstream of the membrane 114, where the membrane 114 defines a transition (i.e., a step) between the first diameter and second diameter. As a result, the pressure applied to the membrane 114 is concentrated in a central portion of the membrane 114 while the physical support is distributed over a larger area. Accordingly, even if the trigger 116 dissolves unevenly the stress on the membrane 114 is concentrated on a central portion of the membrane 114 aligned with the nozzle 112. Thus, when the membrane 114 bursts, the API has a free flow path out of the API reservoir 110 to the outlet 118 where the jet is directed through the outlet 118 without contacting the walls of the outlet 118 prior to impinging on the underlying tissue 200. The rupture process is shown more clearly in FIGS. 2A-2D.

FIGS. 2A-2D depicts a process of actuating a trigger 116 and rupturing a rupturable membrane 114 of a drug delivery device 100. FIG. 2A depicts the drug delivery device 100 in a state prior to ingestion by a subject. In the depicted state, the trigger 116 is configured as a dissolvable plug prior to dissolution in the GI tract. The dissolvable plug occludes and is retained in an outlet 118 of the drug delivery device 100 and supports the rupturable membrane 114. An API reservoir 110 containing pressurized API applies pressure to the membrane 114 on a side of the membrane opposite the trigger 116. In particular, the API applies pressure through an opening of a nozzle 112 of the drug delivery device 100 to the rupturable membrane 114 which may have a downstream opening proximate to the membrane 114 and trigger with a maximum transverse dimension (i.e. diameter) that is smaller than a corresponding maximum transverse dimension of a fluidly connected reservoir 110.

FIGS. 2B and 2C depict stages of the trigger 116 actuation. As shown in FIG. 2B, the trigger 116 has begun to dissolve in the GI tract. According to the embodiment of FIGS. 2A-2D, the dissolvable plug 116 is configured to dissolve more quickly in a center portion of the dissolvable plug (i.e., further from the walls of the outlet 118). Nevertheless, the dissolvable plug 116 may dissolve unevenly relative to a longitudinal centerline of the dissolvable plug due to environmental factors in the GI tract as well as irregularities in the dissolvable plug. As shown in FIG. 2C, the trigger 116 has dissolved further relative to the state shown in FIG. 2B. The trigger 116 had dissolved to an extent where a center portion of the membrane 114 is no longer physically supported by the trigger 116. Accordingly, the membrane 114 bulges under the pressure of the API in the API reservoir 110. As shown in FIG. 2D, the continued dissolution of the trigger 116 ultimately results in the bulge bursting and the API being released from the API reservoir 110 in a jet through the nozzle 112.

As shown in FIGS. 2C-2D, even when the dissolvable plug trigger 116 dissolves unevenly the membrane 114 may rupture in a center portion aligned with the nozzle. As discussed previously, this may be enabled by providing a nozzle 112 having a first diameter smaller than a second diameter of the outlet 118. Accordingly, as the trigger 116 dissolves quickest in a central portion of the dissolvable plug that is spaced away from the walls of the outlet 118, the bulge forms in a portion of the membrane 114 aligned with the nozzle 112. The edges of the membrane 114 remain supported, such that an edge of the membrane 114 does not tear away, which could result in an inefficient or unsatisfactory jet of API. The stress concentration in the center portion of the rupturable membrane 114 also assists in ensuring a clean rupture that does not interfere with the formation of a jet of API from the nozzle 112 that is directed out of the outlet 118 without impinging on the walls of the outlet 118.

According to the embodiment of FIGS. 2A-2D, the dissolvable plug trigger 116 is configured to dissolve more quickly in the center of the trigger 116. To achieve this result, the dissolvable trigger 116 may be potted and polished so that its exterior face exposed to the surrounding environment is both concave and wetted to an outlet of the delivery device. The dissolvable trigger 116 may also be inspected for bubbles, cracks, and incomplete melting, features which may affect the dissolution pattern of the dissolvable trigger. Of course, any suitable arrangement for a dissolvable trigger 116 may be employed, as the present disclosure is not so limited. Additional arrangements for a dissolvable trigger are shown and described with reference to FIGS. 7A-9.

It should be noted that while the embodiment of FIGS. 1A-1B and 2A-2D depict a drug delivery device 100 having a single nozzle 112 and outlet 118, in other embodiments, a drug delivery device 100 may have a plurality of nozzles 112 and/or outlets 118. In some embodiments, a rupturable membrane may be positioned in a flow path upstream of the plurality of nozzles 112 and/or outlets 118. In some cases, including a plurality of outlets 118 in a drug delivery device 100 may improve success rate for penetration of GI tract tissue, as the multiple outlets 118 may compensate for variations in drug delivery device 100 orientation. However, additional outlets may sacrifice payload efficiency, as a single payload may be split between each of the outlets, where only select few of the outlets actually deliver a dose to GI tract tissue. Accordingly, in some embodiments a drug delivery device may include two outlets to improve reliability in view of orientation variations without greatly diminishing payload efficiency. Of course, a drug delivery device may include any suitable number of outlets, as the present disclosure is not so limited.

Figure 3:
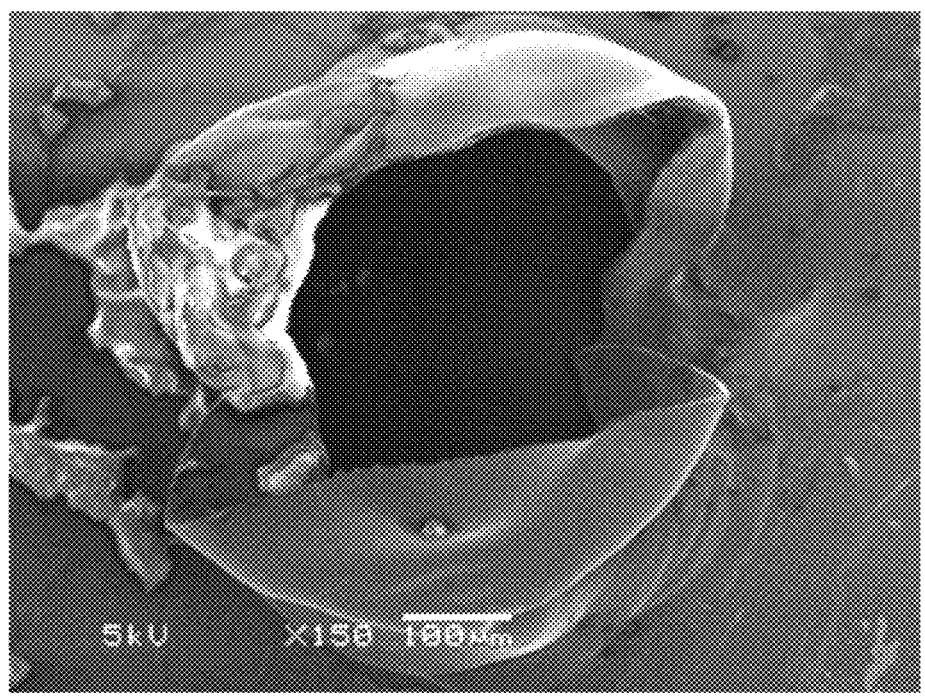
FIG. 3 is a scanning electron micrograph image of one embodiment of a rupturable membrane post-rupture.

FIG. 3 is an SEM image of one embodiment of a rupturable membrane post-rupture. As shown in FIG. 3, an arrangement where a rupturable membrane is ruptured in a center portion of the membrane provides a clean opening through which an API jet may pass cleanly. Accordingly, the API jet may have sufficient energy to pierce GI tract tissue to deliver the API to a subject.

Figure 4A:
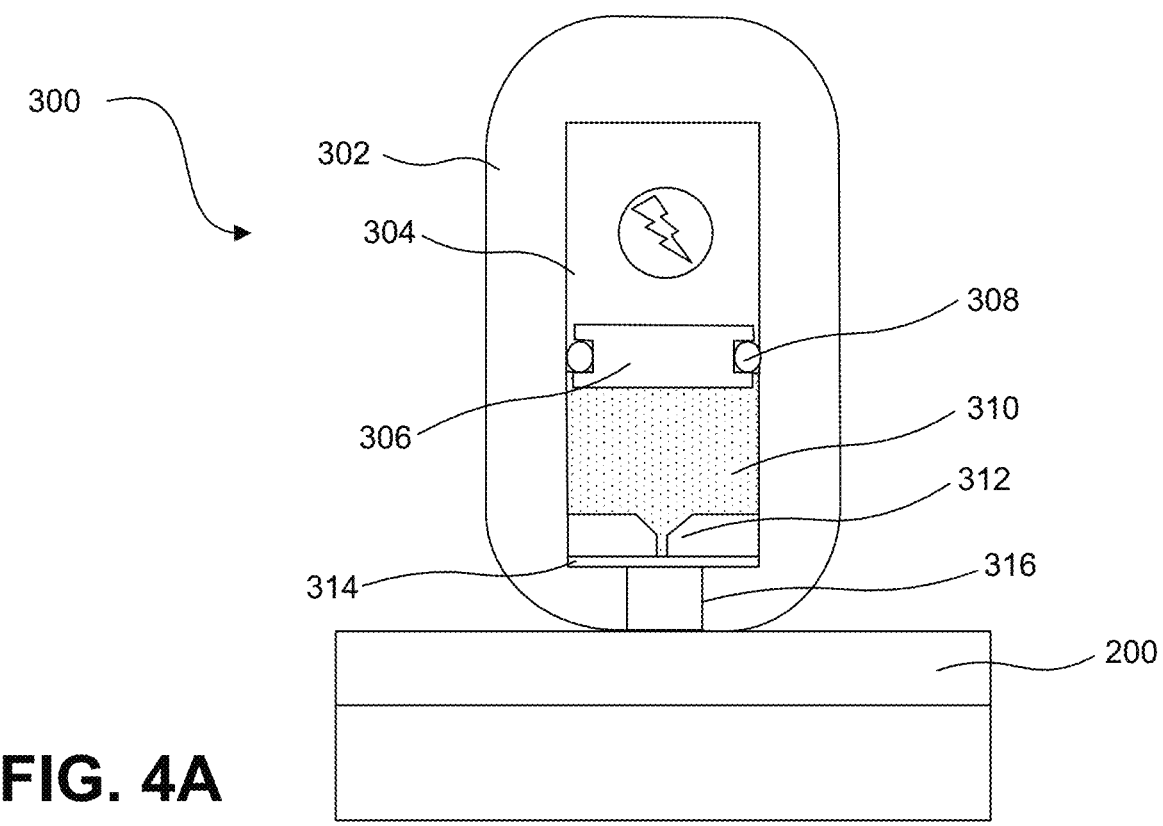
FIG. 4A depicts a schematic of another embodiment of a drug delivery device in a first state.
Figure 4B:
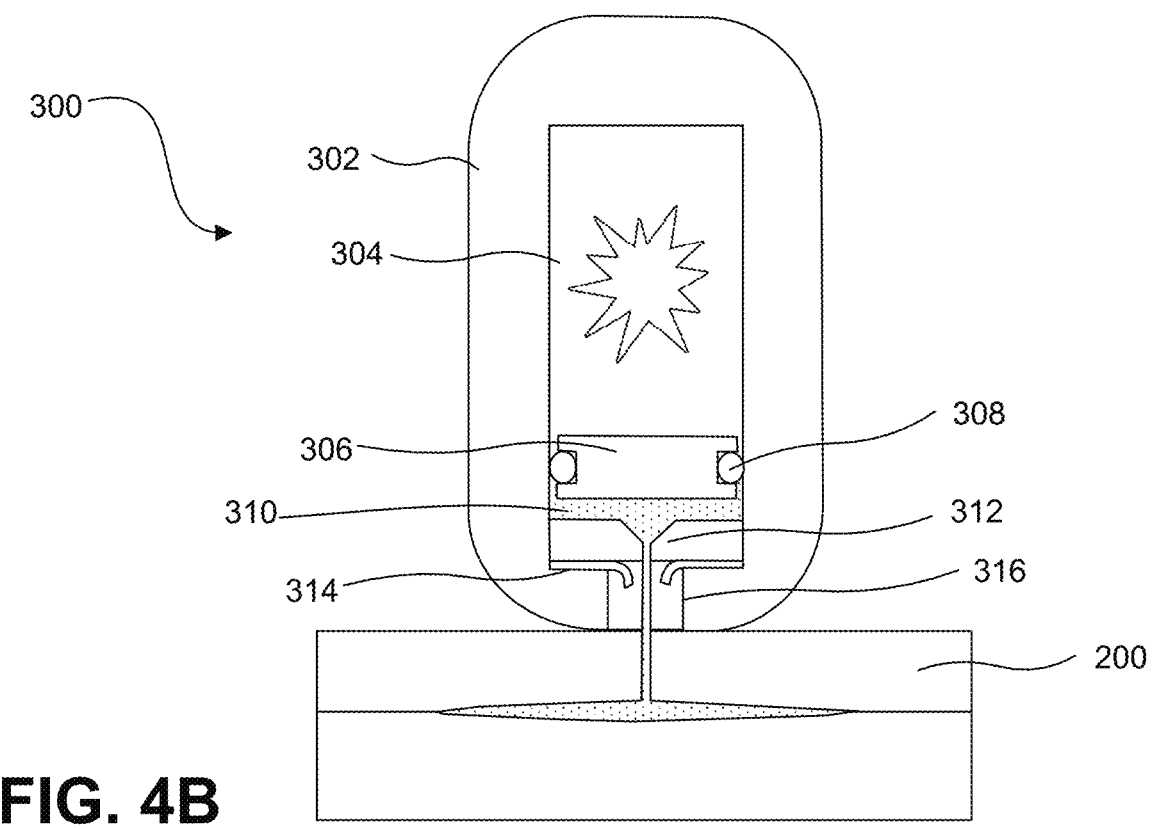
FIG. 4B depicts the drug delivery device of FIG. 4A in a second state.

FIGS. 4A-4B depict a schematic of another embodiment of a drug delivery device 300. According to the embodiment of FIGS. 4A-4B, the trigger is based on a reaction instead of dissolution of a dissolvable plug. As shown in FIG. 4A, the device 300 includes a housing 302 having a reaction chamber 304 and an API reservoir 310. Like the embodiment of FIGS. 1A-1B, the device 300 also includes a piston 306 with a seal 308 configured to transfer pressure between the reaction chamber 304 and the API reservoir 310. The API reservoir 310 is in fluid communication with a nozzle 312. A rupturable membrane 314 is positioned between an outlet 316 and the nozzle 312, and the membrane 314 seals the API inside of the API reservoir 310 until the membrane is ruptured. The device 300 does not include a dissolvable trigger in the outlet 316. The reaction chamber 304 is not pressurized in the state shown in FIG. 4A, such that pressure is not applied to the rupturable membrane 314 in a resting state. Instead, the trigger may be an electrical trigger (e.g., a sensor) and/or a chemical trigger. The reaction chamber 304 may include reactants configured to generate pressure when actuated by the trigger. In some embodiments, an electrical sensor may trigger an acid-base reaction, an explosive reaction, and/or any other appropriate reaction to generate pressurized gas. Of course, any suitable reactants may be used to generate pressure, as the present disclosure is not so limited. Of course, while a dissolving trigger is not used in the embodiment of FIGS. 4A-4B, in other embodiments a dissolving trigger may be employed with a reaction chamber where the dissolvable trigger exposes the reaction chamber 304 to an external gastric environment upon dissolution such that a reactant may react to produce gas when exposed to the gastric environment.

As shown in FIG. 4B, when the reaction is triggered inside of the reaction chamber 304 to pressurize the reaction chamber 304, the piston 306 is forced down to pressurize the API in the API reservoir 310. As there is no dissolvable plug present within the outlet 316 of the device, the membrane 314 is ruptured under the pressure and the API is forced out in a jet with enough power to penetrate GI tract tissue 200 to deliver a therapeutic dose of the API to the patient.

Figure 5A:
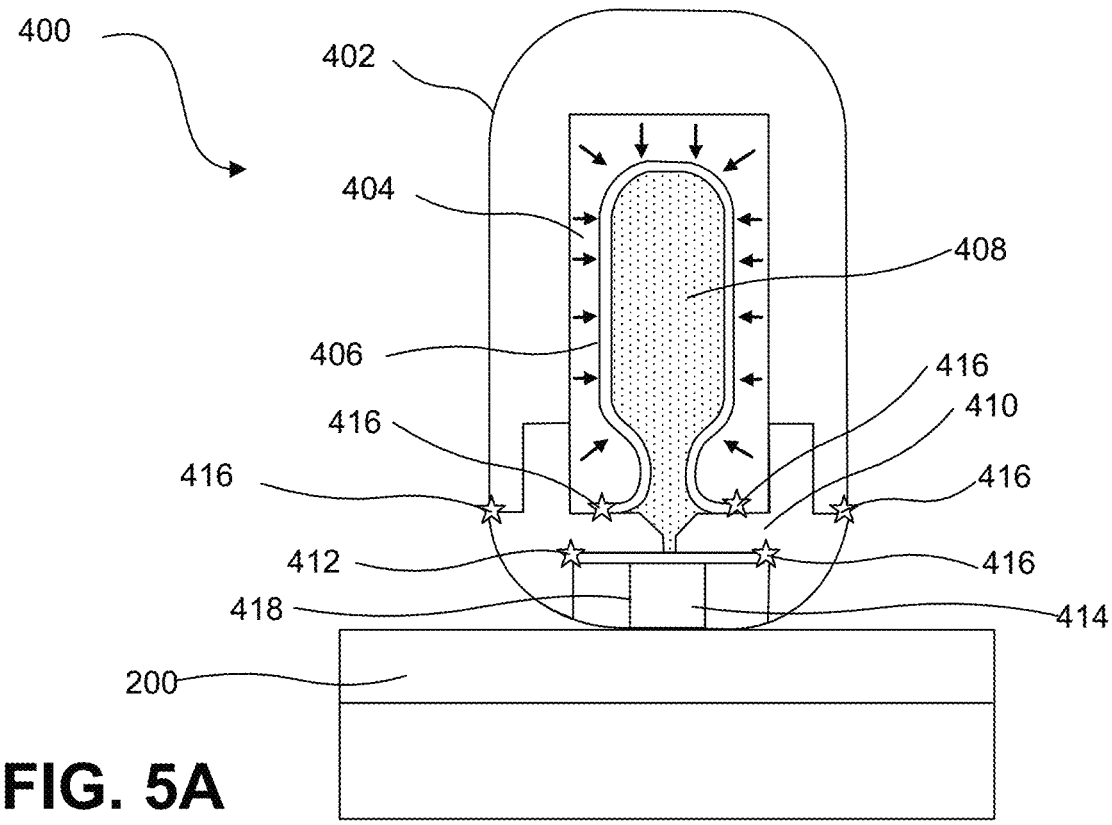
FIG. 5A depicts a schematic of another embodiment of a drug delivery device in a first state.
Figure 5B:
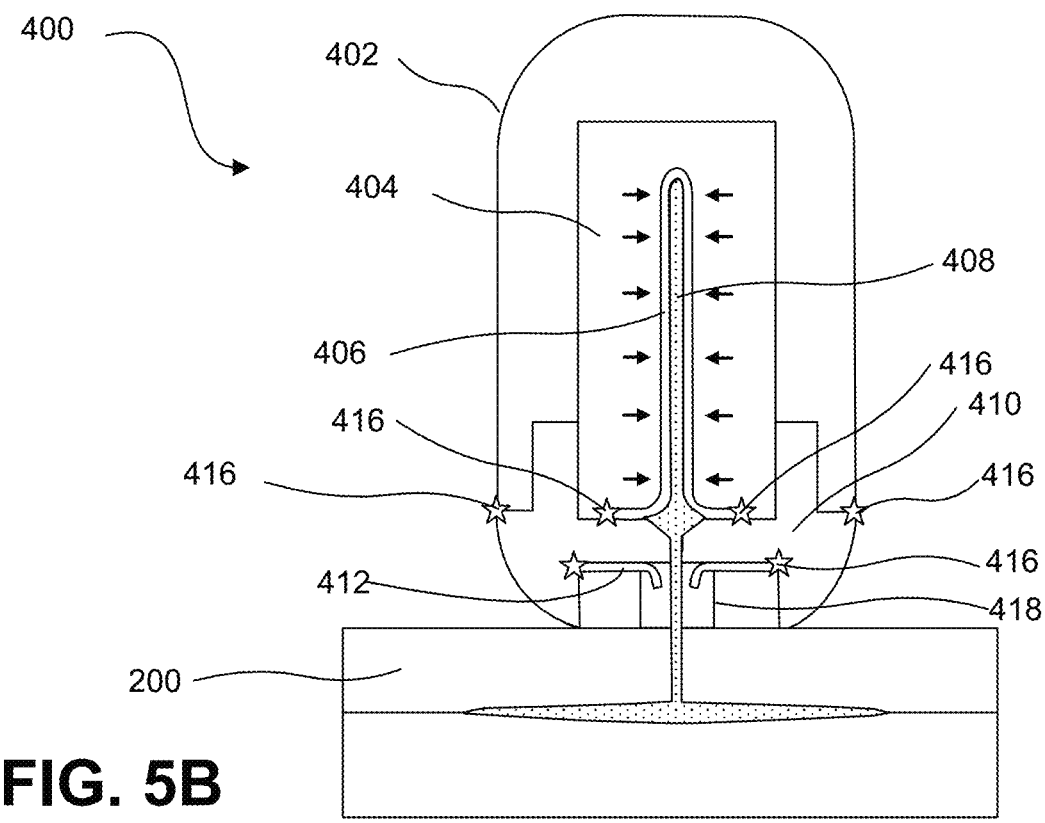
FIG. 5B depicts the drug delivery device of FIG. 5A in a second state.

FIGS. 5A-5B depict a schematic of yet another embodiment of a drug delivery device 400. The embodiment depicted in FIGS. 5A-5B is similar to that of FIGS. 1A-1B, in that the device 400 includes a dissolvable trigger 414 (i.e., a dissolvable plug) configured to actuate the drug delivery device 400. However, in contrast to the prior embodiments, the device 400 of FIGS. 5A-5B does not include a piston, instead the device 400 includes a flexible diffusion barrier 406 configured to allow pressure transmission between a potential energy source and API. As shown in FIG. 5A, the device 400 includes a housing 402 having a gas compartment 404 configured to contain a pressurized gas and an API reservoir 408 configured to contain a solution containing an API. The gas compartment 404 and API reservoir 408 are separated by the flexible diffusion barrier 406, which is configured to maintain separation between the gas compartment 404 and API reservoir 408 while allowing pressure to be transmitted from the gas compartment 404 to the API reservoir 408. A metalized seal 416 may be made between the diffusion barrier 406 and the housing 402 to inhibit diffusion of gas between the gas compartment 404 and the API reservoir 408. Like prior embodiments, the API reservoir 408 is in fluid communication with a nozzle 410 configured to focus the API into a jet. A rupturable membrane 412 is configured to seal the API inside of the API reservoir 408 until the membrane is ruptured. The dissolvable trigger 414 provides physical support for the rupturable membrane 412 and prevents the membrane from rupturing until the trigger 414 dissolves. According to the embodiment of FIGS. 5A-5B, the device 400 also includes a plurality of metalized seals 416 configured to ensure hermetic sealing of fluids within the device 400. In particular, the seals 416 may inhibit diffusion of gas between the various compartments and from inside the housing 402 to an external environment.

As shown in FIG. 5B, when the dissolvable trigger 414 (see FIG. 5A) dissolves, the rupturable membrane 412 may rupture to release the API contained within the API reservoir 408. Pressure applied by compressed gas in the gas compartment 404 (see arrows) forces the API out of the nozzle 410 in a jet. The jet may have a suitable velocity and diameter to puncture GI tract tissue 200 and deliver a dose of the API to the tissue. Like prior embodiments, a diameter of the nozzle 410 upstream of the rupturable membrane 412 is less than a diameter of an outlet channel 418 containing the dissolvable trigger 414. Accordingly, the rupturable membrane 412 ruptures in a center portion aligned with the nozzle 410 such that the rupturable membrane does not significantly interfere with the jet once ruptured.

Figure 6A:
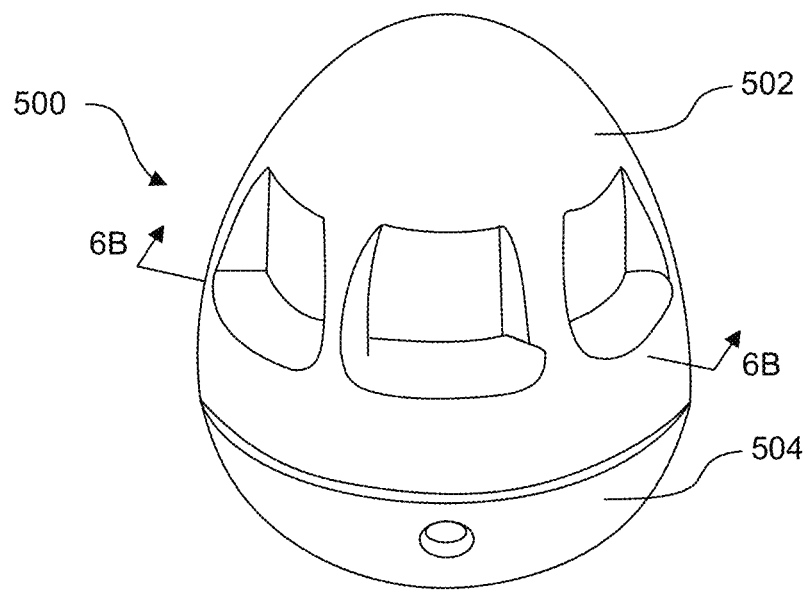
FIG. 6A depicts a perspective view of another embodiment of a drug delivery device.

FIGS. 6A-6D depict various views of another embodiment of a drug delivery device 500 for delivering an API to GI tract mucosal lining tissue in a subject. As shown in FIG. 6A, the device 500 is oval-shaped with a flattened end and may include an upper housing 502 and a lower housing. According to the embodiment of FIGS. 6A-6D, the upper housing 502 and lower housing 504 may be threadedly coupled to one another, as will be discussed below with reference to FIG. 6B. However, embodiments in which the housings are attached to one another using adhesives, welding, brazing, mechanical interferences, and/or any other appropriate attachment method are also contemplated.

Figure 6B:
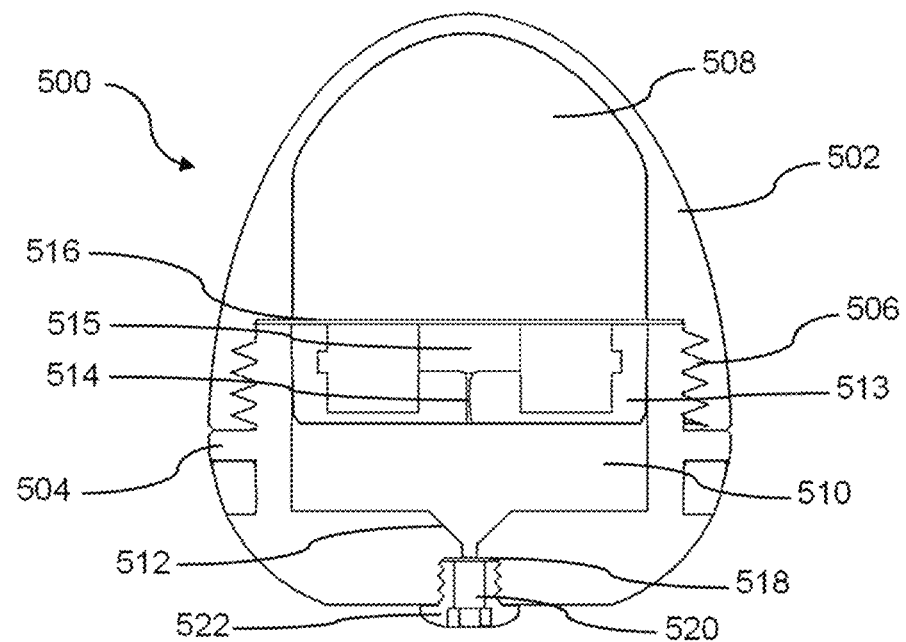
FIG. 6B depicts a cross-sectional view of the drug delivery device of FIG. 6A taken along line 6B-6B.

FIG. 6B depicts a cross-sectional view of the drug delivery device 500 of FIG. 6A taken along line 6B-6B. As shown in FIG. 6B, the upper housing 502 and lower housing 504 are threadedly connected with threads 506. The upper housing 502 contains a gas compartment 508 configured to receive and hold a compressed gas (e.g., a potential energy source). According to the embodiment of FIGS. 6A-6D, the gas compartment 508 is configured to receive dry ice, which may sublimate to provide a predetermined pressure within the gas compartment 508. In this manner, the gas compartment 508 may be filled without an external fill port. Of course, in other embodiments the gas compartment 508 may include a gas fill port and/or may be filled under a pressurized environment, as the present disclosure is not so limited. As shown in FIG. 6B, the lower housing 504 includes an API reservoir 510 and a nozzle 512 in fluid communication with the API reservoir 510. In the depicted embodiment, the nozzle 512 is formed in the lower housing 504. However, embodiments in which a nozzle 512 is a separately formed component assembled with the housing are also contemplated. The lower housing 504 also includes a piston 513 configured to transmit pressure from the compressed gas compartment 508 to the API in the API reservoir 510. According to the embodiment of FIGS. 6A-6D, the piston 513 includes an API fill port 514 and a sealant 515, which allows the API reservoir 510 to be filled when the upper housing 502 is detached from the lower housing 504. The sealant 515 may be applied after the API reservoir 510 is filled to prevent fluid transmission across the piston 513. Like other embodiments discussed herein, the drug delivery device 500 may also include a gas diffusion barrier 516 configured to prevent compressed gas from escaping the gas compartment 508 when stored over long periods of time. The gas diffusion barrier 516 may be a metal barrier and may be configured to break when the device 500 is actuated to release the gas to apply pressure against the piston 513.

According to the embodiment of FIG. 6B, the drug delivery device 500 includes a rupturable membrane 518 positioned adjacent to and disposed against the nozzle 512 and configured to seal the API inside of the API reservoir 510 until the membrane 518 is ruptured. The rupturable membrane 518 is supported by a dissolvable trigger 520 (e.g., a dissolvable plug) so that the membrane 518 does not rupture under the pressure applied by the API through the nozzle. The trigger 520 and rupturable membrane 518 are connected to the lower housing 504 with a trigger plug 522 which is threaded into the lower housing 504. The trigger plug 522 is discussed further below with reference to FIGS. 6C-6D. According to the embodiment of FIG. 6B, the rupturable membrane 518 may be formed of fluorinated ethylene propylene (FEP). Of course, in other embodiments any suitable membrane material may be employed, as the present disclosure is not so limited.

According to the embodiment of FIGS. 6A-6B, a process of filling the drug delivery device 500 includes providing a separate upper housing 502 and lower housing 504. The piston 513 may be placed inside of the lower housing 504, and the trigger plug 522 may be threaded into the lower housing 504. Next, the API reservoir 510 may be filled through the API fill port 514 formed in the piston 513. For example, a pipette or syringe may be used to fill the API reservoir 510 through the API fill port 514. Once the API reservoir 510 is filled, the sealant 515 may be applied to close the API fill port 514. Next, dry ice may be placed in the upper housing 502 along with the diffusion barrier 516, and the upper housing 502 may be threaded onto the lower housing 504 to complete the filling process.

Figure 6C:
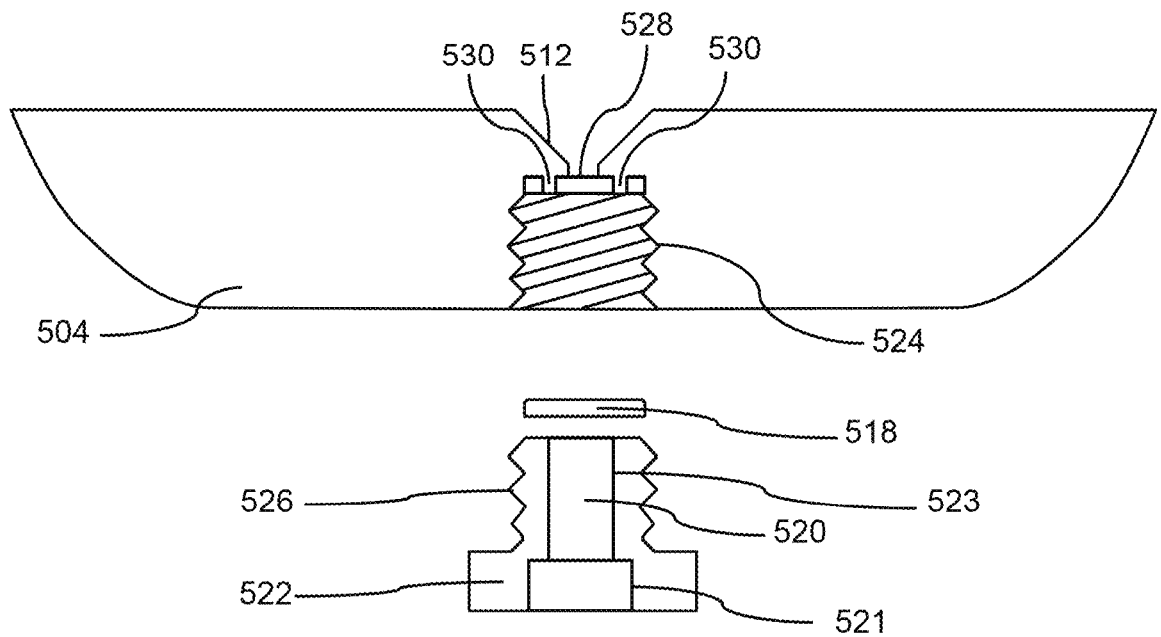
FIG. 6C depicts an enlarged cross-sectional exploded view of a bottom portion of the drug delivery device of FIG. 6B.
Figure 6D:
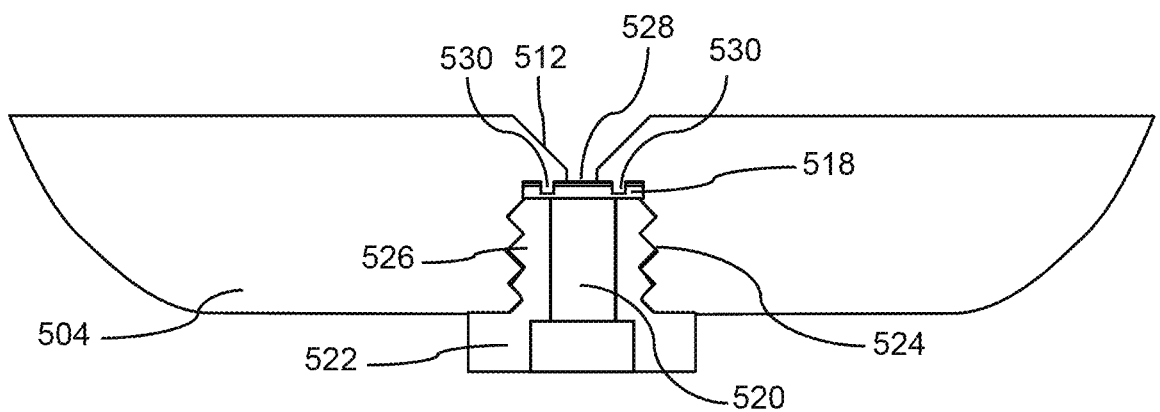
FIG. 6D depicts the enlarged cross-sectional unexploded view of the bottom portion of the drug delivery device of FIG. 6B.

FIG. 6C depicts an enlarged cross-sectional exploded view and FIG. 6D depicts the enlarged cross-sectional unexploded view of a lower portion of the drug delivery device 500 of FIG. 6B. As shown in FIG. 6C, the lower housing 504 includes a nozzle 512 which is in fluid communication with an API reservoir. The lower housing 504 also includes a one or more threads 524 configured to receive the trigger plug 522 which includes a one or more corresponding threads 526. The trigger plug 522 includes an outlet channel 521 and a dissolvable trigger 520 disposed within and retained in an internal channel 523 extending through the trigger plug 522. The trigger 520 is configured to be disposed against and support the rupturable membrane 518 when threaded into the housing 504 until the dissolvable trigger 520 dissolves. As shown in FIGS. 6C and 6D, the lower housing 504 includes a cutout 528 configured to accommodate the membrane 518. The cutout 528 includes one or more sealing protrusions 530 configured to engage the rupturable membrane 518 to form a reliable seal, as shown in FIG. 6D. In the depicted embodiment, the one or more sealing protrusions 530 are provided in the form of a circular protrusion that the sealing plug clamps the membrane 518 against. Without wishing to be bound by theory, variations in surface finish and/or the membrane 518 may affect sealing properties when sealing the membrane 518 against a flat surface. Accordingly, by providing the protrusions 530, a sealing force may be concentrated at the contact locations between the membrane 518 and protrusion 530 to ensure a proper seal is made between the membrane 518 and lower housing 504. By concentrating the sealing pressure away from a center portion of the rupturable membrane 518, the cutout 528 may provide a small cavity above the membrane 518 in which pressurized API may pool and ultimately burst the rupturable membrane 518. Put another way, the API may form a bubble in the center portion of the rupturable membrane 518 so that the membrane ruptures cleanly (i.e., without significant interference with an API jet). Of course, in other embodiment any suitable sealing arrangement for a rupturable membrane 518 may be employed, as the present disclosure is not so limited.

FIGS. 7A-7D depict a schematic of another embodiment of a dissolvable trigger 600 for a drug delivery device undergoing a dissolution process. FIG. 7A depicts the drug delivery device in a state prior to ingestion by a subject. In the depicted state, the trigger 600 is configured as a dissolvable, hollow plug prior to dissolution in the GI tract. The dissolvable plug 600 is retained in an outlet 118 of the drug delivery device and supports the rupturable membrane 114 along an outer radial periphery of the membrane. As shown in FIG. 7A, the dissolvable trigger 600 includes a cylindrical cavity 602 extending the length of the dissolvable trigger. So long as the cavity 602 is suitably narrow so as to not result in a premature membrane rupture, this arrangement of the dissolvable trigger 600 may ensure the membrane 114 ruptures in a center portion of the membrane. As shown in FIG. 7A, an API reservoir 110 containing pressurized API applies pressure to the membrane 114 on a side of the membrane opposite the trigger 600. In particular, the API applies pressure through an opening of a nozzle 112 of the drug delivery device to the rupturable membrane 114. As shown in FIGS. 7B-7D, the dissolvable trigger 600 may dissolve from the cavity 602 outward, resulting in a clean rupture of the membrane 114 shown in FIG. 7D.

Figure 8:
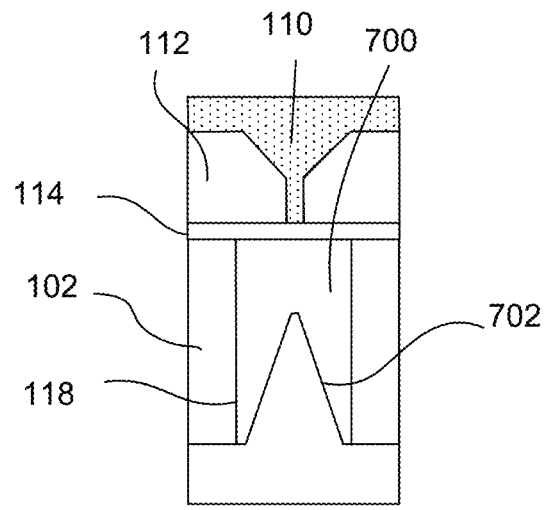
FIG. 8 depicts a schematic of another embodiment of a drug delivery device rupturable membrane and trigger in a first state.

FIG. 8 depicts another schematic of a dissolvable trigger 700 for a drug delivery device. Similar to the embodiment of FIGS. 7A-7D, the drug delivery device of FIG. 8 includes a housing 102, an API reservoir 110, a nozzle 112, and an outlet 118. The dissolvable trigger 700 is configured to physically support the membrane 114 until the dissolvable trigger 700 dissolves in the GI tract. According to the embodiment of FIG. 8, the dissolvable trigger 700 includes a conical cavity 702 which is configured to encourage dissolution of the dissolvable trigger 700 from a center portion of the dissolvable trigger 700 outward.

Figure 9:
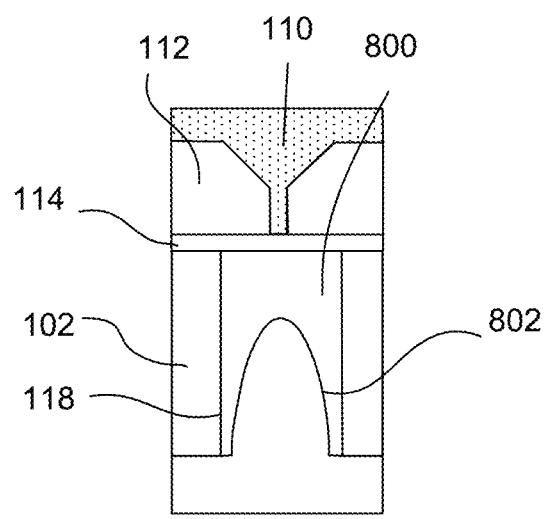
FIG. 9 depicts a schematic of another embodiment of a drug delivery device rupturable membrane and trigger in a first state.

FIG. 9 depicts another schematic of a dissolvable trigger 800 for a drug delivery device. Similar to the embodiment of FIGS. 7A-7D and FIG. 8, the drug delivery device of FIG. 9 includes a housing 102, an API reservoir 110, a nozzle 112, and an outlet 118. The dissolvable trigger 800 is configured to physically support the membrane 114 until the dissolvable trigger 800 dissolves in the GI tract. According to the embodiment of FIG. 8, the dissolvable trigger 800 includes a concave, semi-ellipsoidal cavity 802 which is configured to encourage dissolution of the dissolvable trigger 800 from a center portion of the dissolvable trigger 800 outward.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. An ingestible, insertable, or implantable drug delivery device configured for administration to a subject, the device comprising:
    a reservoir configured to contain an active pharmaceutical ingredient;
    a potential energy source;
    a trigger operatively associated with the potential energy source, the trigger being configured to actuate in response to one or more predetermined conditions;
    an outlet in fluid communication with the reservoir;
    a housing, wherein the reservoir and the potential energy source are disposed in the housing;
    a rupturable membrane disposed along a flow path extending between the reservoir and the outlet, the rupturable membrane sealing the reservoir from the outlet; and
    a nozzle between the rupturable membrane and the reservoir;
    wherein when the trigger is actuated, the potential energy source ruptures the rupturable membrane so that the active pharmaceutical ingredient flows from the reservoir via the flow path, and
    wherein the flow path has a first maximum transverse dimension downstream of the rupturable membrane that is larger than a second maximum transverse dimension of the flow path upstream of the rupturable membrane, and wherein the outlet is formed in the housing and forms the downstream portion of the flow path that has the first maximum transverse dimension.

2. The ingestible, insertable, or implantable drug delivery device of claim 1, wherein when the trigger is actuated, the potential energy source compresses the reservoir to rupture the rupturable membrane so that the active pharmaceutical ingredient flows from the reservoir through the outlet.

3. The ingestible, insertable, or implantable drug delivery device of claim 1, wherein the rupturable membrane ruptures in a center portion of the rupturable membrane.

4. The ingestible, insertable, or implantable drug delivery device of claim 1, wherein the potential energy source comprises at least one of a compressed gas, a spring, and a reaction chamber.

5. The ingestible, insertable, or implantable drug delivery device of claim 1, wherein the trigger is a dissolvable plug configured to dissolve in a gastrointestinal tract of the subject.

6. The ingestible, insertable, or implantable drug delivery device of claim 5, wherein the trigger further comprises an enteric coating.

7. The ingestible, insertable, or implantable drug delivery device of claim 1, wherein the rupturable membrane is a metal foil.

8. The ingestible, insertable, or implantable drug delivery device of claim 1, wherein the rupturable membrane is disposed at a transition between the first maximum transverse dimension and the second maximum transverse dimension.

9. The ingestible, insertable, or implantable drug delivery device of claim 1, wherein an overall volume of the ingestible, insertable, or implantable drug delivery device is less than 3000 mm$^3$.

10. The ingestible, insertable, or implantable drug delivery device of claim 1, wherein an exit portion of the nozzle defines the second maximum transverse dimension, and wherein the second maximum transverse dimension is between 50 μm and 600 μm.

11. The ingestible, insertable, or implantable drug delivery device of claim 10, wherein the second maximum transverse dimension is between 50 μm and 350 μm.

12. The ingestible, insertable, or implantable drug delivery device of claim 1, wherein the flow of the active pharmaceutical ingredient from the reservoir is a jet of the active pharmaceutical ingredient having a sufficient velocity to penetrate tissue proximate to the outlet.

13. The ingestible, insertable, or implantable drug delivery device of claim 1, further comprising a cavity positioned upstream of the rupturable membrane configured to apply pressure in the center portion of the rupturable membrane.

14. The ingestible, insertable, or implantable drug delivery device of claim 1, further comprising a piston configured to apply pressure to the reservoir under force of the potential energy source.

15. The ingestible, insertable, or implantable drug delivery device of claim 14, wherein the potential energy source is a compressed gas, and further comprising a gas diffusion barrier physically supported by the piston and configured to rupture when the rupturable membrane ruptures.

16. An ingestible, insertable, or implantable drug delivery device configured for administration to a subject, the device comprising:
    a reservoir configured to contain an active pharmaceutical ingredient;
    a potential energy source;
    a trigger operatively associated with the potential energy source, the trigger being configured to actuate in response to one or more predetermined conditions;
    an outlet in fluid communication with the reservoir;
    a housing, wherein the reservoir and the potential energy source are disposed in the housing; and
    a rupturable membrane disposed along a flow path extending between the reservoir and the outlet, the rupturable membrane sealing the reservoir from the outlet;
    wherein when the trigger is actuated, the potential energy source ruptures the rupturable membrane so that the active pharmaceutical ingredient flows from the reservoir via the flow path, and
    wherein the flow path has a first maximum transverse dimension downstream of the rupturable membrane that is larger than a second maximum transverse dimension of the flow path upstream of the rupturable membrane, and wherein the outlet is formed in the housing and forms the downstream portion of the flow path that has the first maximum transverse dimension, and
    wherein when the rupturable membrane ruptures, a jet of the active pharmaceutical ingredient is directed through the outlet without contacting the walls of the outlet.

17. The ingestible, insertable, or implantable drug delivery device of claim 16, wherein when the trigger is actuated, the potential energy source compresses the reservoir to rupture the rupturable membrane so that the active pharmaceutical ingredient flows from the reservoir through the outlet.

18. The ingestible, insertable, or implantable drug delivery device of claim 16, wherein the rupturable membrane ruptures in a center portion of the rupturable membrane.

19. The ingestible, insertable, or implantable drug delivery device of claim 16, wherein the potential energy source comprises at least one of a compressed gas, a spring, and a reaction chamber.

20. The ingestible, insertable, or implantable drug delivery device of claim 16, wherein the trigger is a dissolvable plug configured to dissolve in a gastrointestinal tract of the subject.

21. The ingestible, insertable, or implantable drug delivery device of claim 20, wherein the trigger further comprises an enteric coating.

22. The ingestible, insertable, or implantable drug delivery device of claim 16, wherein the rupturable membrane is a metal foil.

23. The ingestible, insertable, or implantable drug delivery device of claim 16, wherein the rupturable membrane is disposed at a transition between the first maximum transverse dimension and the second maximum transverse dimension.

24. The ingestible, insertable, or implantable drug delivery device of claim 16, wherein an overall volume of the ingestible, insertable, or implantable drug delivery device is less than 3000 mm$^3$.

25. The ingestible, insertable, or implantable drug delivery device of claim 16, further comprising a nozzle between the rupturable membrane and the reservoir, wherein an exit portion of the nozzle defines the second maximum transverse dimension, and wherein the second maximum transverse dimension is between 50 μm and 600 μm.

26. The ingestible, insertable, or implantable drug delivery device of claim 25, wherein the second maximum transverse dimension is between 50 μm and 350 μm.

27. The ingestible, insertable, or implantable drug delivery device of claim 16, wherein the flow of the active pharmaceutical ingredient from the reservoir is a jet of the active pharmaceutical ingredient having a sufficient velocity to penetrate tissue proximate to the outlet.

28. The ingestible, insertable, or implantable drug delivery device of claim 16, further comprising a cavity positioned upstream of the rupturable membrane configured to apply pressure in the center portion of the rupturable membrane.

29. The ingestible, insertable, or implantable drug delivery device of claim 16, further comprising a piston configured to apply pressure to the reservoir under force of the potential energy source.

30. The ingestible, insertable, or implantable drug delivery device of claim 29, wherein the potential energy source is a compressed gas, and further comprising a gas diffusion barrier physically supported by the piston and configured to rupture when the rupturable membrane ruptures.

31. An ingestible, insertable, or implantable drug delivery device configured for administration to a subject, the device comprising:
  a reservoir configured to contain an active pharmaceutical ingredient;
  a potential energy source;
  a trigger operatively associated with the potential energy source, the trigger being configured to actuate in response to one or more predetermined conditions;
  an outlet in fluid communication with the reservoir;
  a housing, wherein the reservoir and the potential energy source are disposed in the housing; and
  a rupturable membrane disposed along a flow path extending between the reservoir and the outlet, the rupturable membrane sealing the reservoir from the outlet;
  wherein when the trigger is actuated, the potential energy source ruptures the rupturable membrane so that the active pharmaceutical ingredient flows from the reservoir via the flow path, and
  wherein the flow path has a first maximum transverse dimension downstream of the rupturable membrane that is larger than a second maximum transverse dimension of the flow path upstream of the rupturable membrane, and wherein the outlet is formed in the housing and forms the downstream portion of the flow path that has the first maximum transverse dimension, and
  wherein the flow path upstream of and adjacent to the rupturable membrane has a maximum transverse dimension that is less than a maximum transverse dimension of the membrane.

32. The ingestible, insertable, or implantable drug delivery device of claim 31, wherein when the trigger is actuated, the potential energy source compresses the reservoir to rupture the rupturable membrane so that the active pharmaceutical ingredient flows from the reservoir through the outlet.

33. The ingestible, insertable, or implantable drug delivery device of claim 31, wherein the rupturable membrane ruptures in a center portion of the rupturable membrane.

34. The ingestible, insertable, or implantable drug delivery device of claim 31, wherein the potential energy source comprises at least one of a compressed gas, a spring, and a reaction chamber.

35. The ingestible, insertable, or implantable drug delivery device of claim 31, wherein the trigger is a dissolvable plug configured to dissolve in a gastrointestinal tract of the subject.

36. The ingestible, insertable, or implantable drug delivery device of claim 35, wherein the trigger further comprises an enteric coating.

37. The ingestible, insertable, or implantable drug delivery device of claim 31, wherein the rupturable membrane is a metal foil.

38. The ingestible, insertable, or implantable drug delivery device of claim 31, wherein the rupturable membrane is disposed at a transition between the first maximum transverse dimension and the second maximum transverse dimension.

39. The ingestible, insertable, or implantable drug delivery device of claim 31, wherein an overall volume of the ingestible, insertable, or implantable drug delivery device is less than 3000 mm$^3$.

40. The ingestible, insertable, or implantable drug delivery device of claim 31, further comprising a nozzle between the rupturable membrane and the reservoir, wherein an exit portion of the nozzle defines the second maximum transverse dimension, and wherein the second maximum transverse dimension is between 50 μm and 600 μm.

41. The ingestible, insertable, or implantable drug delivery device of claim 40, wherein the second maximum transverse dimension is between 50 μm and 350 μm.

42. The ingestible, insertable, or implantable drug delivery device of claim 31, wherein the flow of the active pharmaceutical ingredient from the reservoir is a jet of the active pharmaceutical ingredient having a sufficient velocity to penetrate tissue proximate to the outlet.

43. The ingestible, insertable, or implantable drug delivery device of claim 31, further comprising a cavity positioned upstream of the rupturable membrane configured to apply pressure in the center portion of the rupturable membrane.

44. The ingestible, insertable, or implantable drug delivery device of claim 31, further comprising a piston configured to apply pressure to the reservoir under force of the potential energy source.

45. The ingestible, insertable, or implantable drug delivery device of claim 44, wherein the potential energy source is a compressed gas, and further comprising a gas diffusion barrier physically supported by the piston and configured to rupture when the rupturable membrane ruptures.

\* \* \* \* \*